US00PP30989P2

(12) United States Plant Patent
Klemm et al.

(10) Patent No.: US PP30,989 P2
(45) Date of Patent: Oct. 29, 2019

(54) ***DIANTHUS* PLANT NAMED 'KLEDP18255'**

(50) Latin Name: *Dianthus caryophyllus*
Varietal Denomination: KLEDP18255

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/350,181

(22) Filed: Oct. 10, 2018

(51) Int. Cl.
*A01H 5/02* (2018.01)
*A01H 6/30* (2018.01)

(52) U.S. Cl.
USPC ..... Plt./274

(58) Field of Classification Search
USPC ..... Plt./272, 273, 274
See application file for complete search history.

*Primary Examiner* — Susan McCormick Ewoldt
(74) *Attorney, Agent, or Firm* — Bethany R. Roahrig; Cochran Freund & Young LLC

(57) ABSTRACT

A new *Dianthus* plant particularly distinguished by large, double white flowers, and an upright habit, is disclosed.

1 Drawing Sheet

Genus and species: *Dianthus caryophyllus*.
Variety denomination: 'KLEDP18255'.

CROSS REFERENCE TO RELATED APPLICATION

A Canadian Plant Breeders Rights Application for this variety was filed on Apr. 27, 2018, Application No. 18-9429. 'KLEDP18255' has not been sold or made publicly available more than one year prior to the filing date of the present application.

BACKGROUND OF THE NEW PLANT

The present invention comprises a new and distinct variety of *Dianthus*, botanically known as *Dianthus caryophyllus*, and hereinafter referred to by the variety name 'KLEDP18255'. 'KLEDP18255' originated from a cross pollination of the proprietary female parent 'DCP-2006-0024' (unpatented) and the proprietary male parent 'DCP-2009-0069' (unpatented) in June 2013, in Stuttgart, Germany.

In July 2014, a single plant was selected. In September 2014, 'KLEDP18255' was first vegetatively propagated by vegetative cuttings in Stuttgart Germany. 'KLEDP18255' was found to reproduce true to type in successive generations of asexual propagation in Latina, Italy via vegetative stem cuttings.

SUMMARY

The following are the most outstanding and distinguishing characteristics of this new variety when grown under normal horticultural practices in Stuttgart, Germany.

1. Large, double white flowers; and
2. An upright habit.

DESCRIPTION OF THE PHOTOGRAPH

This new *Dianthus* plant is illustrated by the accompanying photograph of a plant approximately 9 weeks old and grown in a greenhouse in Stuttgart, Germany. The photograph shows the whole plant, including the flowers and foliage and buds and was taken in April 2015 in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEDP18255'. The data which define these characteristics were collected from asexual reproductions carried out in Stuttgart, Germany. Data was collected in April 2018 on 6-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP18255'.

Parentage:
- *Female parent*.—The proprietary *Dianthus* variety 'DCP-2006-0024' (unpatented).
- *Male parent*.—The proprietary *Dianthus* variety 'DCP-2009-0069' (unpatented).

Plant:
- *Plant form*.—Upright.
- *Plant height*.—14.0 cm to 16.0 cm.
- *Plant diameter or spread*.—18.0 cm to 20.0 cm.
- *Propagation type*.—Vegetative cuttings, stem cutting.
- *Time to produce a rooted young plant*.—10 to 14 days.
- *Root description*.—White, fine.
- *Rooting habit (shape)*.—Lanceolate.

Lateral branches:
- *Number of lateral branches*.—7.
- *Strength*.—Normal.
- *Length*.—12.0 cm to 14.0 cm.
- *Diameter*.—4.0 mm to 6.0 mm.

*Internode length.*—2.0 cm to 3.0 cm.
*Number of internodes per branch/stem.*—4 to 6.
*Node length.*—0.3 cm to 0.5 cm.
*Node diameter.*—0.3 cm to 0.5 cm.
*Texture.*—Smooth.
*Color.*—RHS 139A.
*Branch/stem appearance.*—Solid.

Foliage:
*Arrangement.*—Opposite.
*Length.*—4.0 cm to 6.0 cm.
*Width.*—0.5 cm to 0.8 cm.
*Shape.*—Lanceolate.
*Apex.*—Acute.
*Base.*—Obtuse.
*Margin.*—Entire.
*Texture (both upper and lower surfaces).*—Smooth.
*Immature leaf color.*—Upper surface: RHS 137A. Lower surface: RHS 137B.
*Mature leaf color.*—Upper surface: RHS 139A. Lower surface: RHS 137A.
*Venation pattern.*—Parallel.
*Venation color.*—Upper surface: RHS 139A. Lower surface: RHS 137A.

Flowers:
*Flower type and habit.*—Double flower, small sprays.
*Fragrance.*—Present, typical of a carnation.
*Natural flowering season.*—Spring to fall.
*Position of flowers relative to the foliage.*—Moderately above.
*Number of flowers per spray.*—3 to 4.
*Flower longevity on the plant.*—10 to 12 days.
*Buds.*—Length: 1.5 cm to 2.0 cm. Diameter: 1.0 cm to 1.5 cm. Shape: Elliptic. Color: Apical part is RHS N137B and basal part is RHS 144C. Extrusion of the styles at the bud stage: Absent.
*Corolla.*—Quantity of petals and arrangement: 20 to 25 in whorls. Corolla height: 1.5 cm to 2.0 cm. Corolla diameter: 3.0 cm. Petal length: 3.0 cm to 4.0 cm. Petal width: 1.6 cm to 2.0 cm. Petal shape: Spoon-shaped. Petal apex: Obtuse. Petal base: Acute. Petal margin: Crenate. Depth of petal margin: Medium. Petal texture (both upper and lower surfaces): Smooth. Petal luster: Upper surface: Dull. Lower surface: Light and shiny. Petal color: Immature: Upper surface: RHS NN155B; in summer, a light pink eye colored RHS 58C. Lower surface: RHS NN155B. Mature: Upper surface: RHS NN155B; in summer, a light pink eye colored RHS 58C. Lower surface: RHS NN155B.
*Calyx.*—Quantity of sepals and arrangement: Composed of 5 sepals, fused. Shape: Campanulate. Calyx height: 1.5 cm to 2.0 cm. Calyx diameter (at the apex): 1.0 cm to 1.5 cm. Sepal texture (both upper and lower surfaces): Smooth. Sepal color: Upper surface: RHS 137A. Lower surface: RHS 137D. Sepal length: 2.0 cm. Sepal diameter: 1.0 cm. Sepal apex: Acute. Sepal base: Obtuse. Sepal margin: Entire. Sepal luster (both surfaces): Dull.

Peduncles:
*Length.*—13.0 cm to 14.0 cm.
*Diameter.*—0.2 cm to 0.3 cm.
*Strength.*—Moderate.
*Texture.*—Smooth.
*Color.*—RHS N137B.

Reproductive organs:
*Stamens.*—Quantity per flower: 4 to 7. Filament length: 0.7 cm to 1.0 cm. Filament color: RHS 157C. Anther length: 0.1 cm. Anther diameter: 0.05 cm. Anther color: RHS 160B. Pollen amount: Sparse.
*Pistils.*—Quantity per flower: 1. Pistil length: 1.5 cm to 2.0 cm. Style length: 1.0 cm to 1.3 cm. Style color: RHS 155C. Stigma shape: Filamentous. Stigma color: RHS 155C. Ovary size: 0.8 cm to 1.0 cm. Ovary shape: Oval. Ovary color: Basal part is RHS 145C and the apical part is RHS 144C.

Fruit and seed set: Seed is sometimes observed, but no information on the seed is available.

Disease and pest/insect resistance: No disease and pest/insect resistance observed.

COMPARISON WITH PARENTAL LINES AND KNOWN VARIETY

'KLEDP18255' is distinguished from its female parent as described in Table 1.

TABLE 1

Comparison with Parental Lines

| Characteristic | 'KLEDP18255' | Female Parent 'DCP-2006-0024' | Male Parent 'DCP-2009-0069' |
|---|---|---|---|
| Number of petals | Strong filling, big flowers; more petals than 'DCP-2006-0024' and 'DCP-2009-0069' | Fewer petals than 'KLEDP18255' | Fewer petals than 'KLEDP18255' |

'KLEDP18255' can be compared to the commercial *Dianthus* variety 'KLEDP08098' (European Community Plant Variety Protection Application No. 2009/1174). Differences between the varieties are described in Table 2.

TABLE 2

Comparison with Similar Variety

| Characteristic | 'KLEDP18255' | 'KLEDP08098' |
|---|---|---|
| Flower size | Large flower, strong filling | Smaller flower than 'KLEDP18255' and less filling |

We claim:

1. A new and distinct variety of *Dianthus* plant designated 'KLEDP18255' as illustrated and described herein.

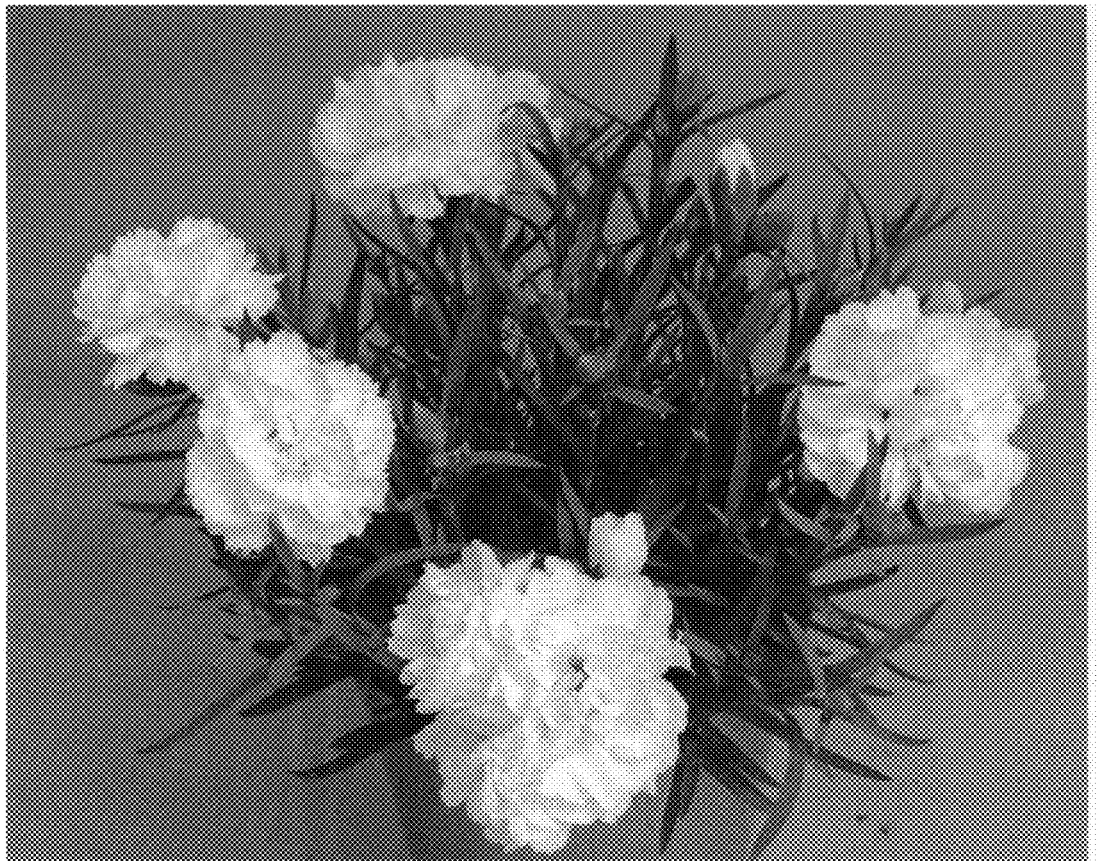

* * * * *